(12) United States Patent
Wise

(10) Patent No.: US 6,642,370 B1
(45) Date of Patent: Nov. 4, 2003

(54) GENETIC MARKER FOR AUTOIMMUNE DISORDER

(75) Inventor: Carol A. Wise, Dallas, TX (US)

(73) Assignee: Texas Scottish Rite Hospital for Children, Dallas, TX (US)

( * ) Notice: Subject to any disclaimer, the term of this patent is extended or adjusted under 35 U.S.C. 154(b) by 274 days.

(21) Appl. No.: 09/710,693

(22) Filed: Nov. 8, 2000

(51) Int. Cl.$^7$ ................................................ C07H 21/04
(52) U.S. Cl. .................. 536/23.6; 435/69.1; 435/320.1; 435/325
(58) Field of Search ........................ 536/23.6; 435/69.1, 435/320.1, 325

(56) References Cited

PUBLICATIONS

Yeon et al., "Pyogenic Arthritis, Pyoderma Gangrenosum, and Acne Syndrome Maps to Chromosome 15q," Am. J. Hum. Genet. 66:000–000, 2000.

Dowbenko et al., "Identification of a Novel Polyproline Recognition Site in the Cytoskeletal Associated Protein, Proline Serine Threonine Phosphatase Interacting Protein," Journal of Biol. Chem., 273(2):989–96, 1998.

Heward and Gough, "Genetic susceptibility to the development of autoimmune disease," Clinical Science 93:479–91, 1997.

Jacobs and Goetzl, "'Streaking Leukocyte Factor,' Arthritis, and Pyoderma Gangrenosum", Pediatrics, 56(4)570–78, 1975.

Kammerer, et al., "Biliary glycoproetin (CD66a), a cell adhesion molecule of the immunoglobulin superfamily, on human lymphocytes: structure, expression and involvement in T cell activaction," Eur. J. Immunol. 28:3664–74, 1998.

Li, et al., "A cdc15–like adaptor protein (CD2BP1) interacts with the CD2 cytoplasmic domain and regulates CD2–triggered adhesion," The EMBO Journal, 17(24):7320–36, 1998.

Lindor, et al., "A New Autosomal Dominant Disorder of Pyogenic Sterile Arthritis, Pyoderma Gangrenosum, and Acne: PAPA Syndrome," Mayo Clin. Proc. 72:611–15, 1997.

Lucka, et al., "Carcinoembryonic antigen–related cell–cell adhesion molecule C–CAM is greatly increased in serum and urine of rats with liver diseases," FEBS Letters 438:37–40, 1998.

Moroldo, et al., "Transmission Disequilibrium as a Test of Linkage and Association between HLA Alleles and Pauciarticular–Onset Juvenile Rheumatoid Arthritis," Arthritis & Rheumatism 41(9):1620–24, 1998.

Murray, et al., "Pathogenesis of juvenile chronic arthritis: genetic and environmental factors," Archives of Disease in Childhood 77:530–34, 1997.

Rossen, et al., "Linkage of HLA to Disease Susceptibility Locus in Four Families where Proband Presented with Juvenile Rheumatoid Arthritis," J. Clin. Invest. 65:629–42, 1980.

Rossen, et al., "Familial Rheumatoid Arthritis: A Kindred Identified Through a Proband with Seronegative Juvenile Arthritis Includes Members with Seropositive, Adult–Onset Disease," Human Immunology, 4:183–96, 1982.

Spencer, et al., "PSTPIP: A Tyrosine Phosphorylated Cleavage Furrow–associated Protein that Is a Substrate for a PEST Tyrosine Phosphatase," Journal of Cell Biology, 138(4):845–60, 1997.

Stocks, et al., "Expression of the CD 15 differentiation antigen (3–fucosyl–N–acetyl–lactosamine, Lex) on putative neutrophil adhesion molecules CR3 and NCA–160," Biochem J. 268:275–80, 1990.

Stocks and Kerr, "Stimulation of neutrophil adhesion by antibodies recognizing CD15 (LeX) and CD15–expressing carcinoembryonic antigen–related glycoprotein NCA–160," Biochem J. 288:23–27, 1992.

Vyse and Todd, "Genetic Analysis of Autoimmune Disease," Cell, 85:311–18, 1996.

Warren, et al., "A Carbohydrate Structure Associated with CD15 (Lewis–x) on Myeloid Cells Is a Novel Ligand for Human CD2," J. Immunology, 156:2866–73, 1996.

Wise, et al., "Localization of a Gene for Familial Recurrent Arthritis," Arthritis & Rheumatism, 43(9):2041–45, 2000.

Wu, et al., "Tyrosine Phosphorylation Regulates the SH3–mediated Binding of the Wiskott–Aldrich Syndrome Protein to PSTPIP, a Cytoskeletal–associated Protein," The Journal of Biological Chemistry, 273(10):5765–70, 1998.

*Primary Examiner*—Patrick J. Nolan
(74) *Attorney, Agent, or Firm*—Vinson & Elkins L.L.P.

(57) ABSTRACT

A mutation in an allele of the gene encoding the CD2BP1 protein is identified as a causative factor in familial recurrent arthritis. Methods of diagnosis and methods of screening for effectors of the mutated protein binding and function are disclosed.

9 Claims, 1 Drawing Sheet

FIG. 1

```
CD2BP1  MMPQLQFKDA  FWCRDFTAHT  GYEVLLQRLL  DGRKMCKDME  ELLRQRAQAE   50
PSTPIP  MMAQLQFRDA  FWCRDFTAHT  GYEVLLGRLL  DGRKMCKDVE  ELLRQRAQAE

CD2BP1  ERYGKELVQI  ARKAGGQTEI  NSLRASFDSL  KQQMENVGSS  HIQLALTLRE  100
PSTPIP  ERYGKELVQI  ARKAGGQTEM  NSLRTSFDSL  KQQTENVGSA  HIQLALALRE

CD2BP1  ELRSLEEFRE  RQKEQRKKYE  AVMDRVQKSK  LSLYKKAMES  KKTYEQKCRD  150
PSTPIP  ELRSLEEFRE  RQKEQRKKYE  AIMDRVQKSK  LSLYKKTMES  KKAYDQKCRD

CD2BP1  ADDAEQAFER  ISANGHQKQV  EKSQNKARQC  KDSATEAERV  YRQSIAQLEK  200
PSTPIP  ADDAEQAFER  VSANGHQKQV  EKSQNKAKQC  KESATEAERV  YRGNIEQLER

CD2BP1  VRAEWEQEHR  TTCEAFQLQE  FDRLTILRNA  LWVHSNQLSM  QCVKDDELYE  250
PSTPIP  ARTEWEQEHR  TTCEAFQLQE  FDRLTILRNA  LWVHCNQLSM  QCVKDDELYE

CD2BP1  EVRLTLEGCS  IDADIDSFIQ  AKSTGTEPPA  PVPYQNYYDR  EVTPLTSSPG  300
PSTPIP  EVRLTLEGCD  VEGGDINGFIQ SKSTGREPPA  PVPYQNYYDR  EVTPLIGSPS

CD2BP1  IQPSCGMIKR  FSGLLHGSPK  TTSLAASAAS  TETLTPTPER  NEGVYTAIAV  350
PSTPIP  IQPSCGVIKR  FSGLLHGSPK  TTP–SAPAAS  TETLTPTPER  NELVYASIEV

CD2BP1  QEIQGNPASP  AQEYRALYDY  TAQNPDELDL  SAGDILEVIL  EGEDGWWTVE  400
PSTPIP  QATQGNLNSS  AQDYRALYDY  TAQNSDELDI  SAGDILAVIL  EGEDGWWTVE

CD2BP1  RNGQRGFVPG  SYLEKL                                            416
PSTPIP  RNGQRGFVPG  SYLEKL
```

GENETIC MARKER FOR AUTOIMMUNE DISORDER

BACKGROUND

1. Field of the Invention

The present invention is related to the field of inherited immunological disorders and to the discovery of a genetic mutation as a causative factor in a disorder. The invention also relates to genetic screening for inherited disease and in particular for a marker for familial recurrent arthritis.

2. Description of Related Art

Juvenile idiopathic arthritis (JIA), also known as juvenile rheumatoid arthritis (JRA), is an autoimmune disorder comprising a heterogeneous collection of chronic arthritis of childhood (Fink et al., 1995, *Pediatr Clin North Am* 42:1155). This disease is common and affects 1–3 children per 1000. The pathogenesis of JIA as a whole is poorly understood, although genetics has been proposed to play a causative role. (Murray et al., 1997 *Arch Dis Child* 77:530; Moroldo et al., 1998, *Arthritis Rheum* 41:1620; Rossen et al., 1980, *J. Clin Invest* 65:629; Rossen et al., 1982, *Human Immunol* 4:183). For pauciarticular onset JIA, in which the arthritis is limited to 4 or fewer joints during the first 6 months of disease, both family and population-based studies have revealed linkage and association with specific HLA alleles and disease. Associations with other immune complex molecules are also described (Heward and Gough, 1997, *Clin Sci* 93:479). There is, in addition, a striking gender effect for pauci-onset, with a ratio of approximately 8 to 1 girls to boys. Taken altogether the evidence for genetic predisposition to pauci-onset JIA is strong. However, a single causative gene has yet to be identified.

JIA is similar to other autoimmune disorders in that each appears to arise from complex genetic and environmental interactions (Heward and Gough, 1997; Vyse and Todd, 1996, *Cell* 85:311). Delineation of these factors and their mechanisms of action is ultimately critical to an understanding of the causes of the destruction of the body's own tissues. One approach to the genetic dissection of these complex disorders is positional cloning of predisposing genes within kindreds who demonstrate a simpler inheritance pattern, a strategy which has been successful in mapping and cloning genes involved in common diseases such as psoriasis (Tomfohrde et al., 1994, *Science* 264:1141), familial breast cancer (Hall, J M, et al., 1990, *Science* 250:1684) and early onset Alzheimer's disease (St. George-Hyslop et al., 1992, *Nat Genet* 2:330).

The present inventor has described a new disorder that occurs in a subset of patients diagnosed as having juvenile idiopathic arthritis. This disorder has been termed "familial recurrent arthritis" or "FRA," and was identified in a single large family originally carrying the diagnosis of JIA. FRA differs from "classic" JIA in several ways, but most notably in its striking pattern of dominant inheritance, in the pyogenic component of the joint swelling, and in the association with cutaneous findings. A genome wide linkage scan identified a 20 cM region within 15q22–24 most likely to harbor the predisposing gene.

Another disorder with striking similarity to FRA has been reported (Lindor et al., 1997, Mayo *Clin Proc* 72:611). The authors reported a single extended family with autosomal dominant transmission of a disorder characterized by pyogenic sterile arthritis, pyoderma gangrenosum, and severe cystic acne which they referred to as "PAPA syndrome". Like FRA, PAPA syndrome patients presented with acute inflammations which responded to steroid treatment, and laboratory findings were negative. Nine out of ten affected individuals in the PAPA syndrome family were reported to have arthritis in one to three joints, with age of onset varying from one to 16 years of age. Dermatological manifestations were variously found including pyoderma gangrenosum and severe cystic acne with onset at 11 years of age. The PAPA family was also reported to be karyotypically normal, and preliminary genotyping detected no linkage to the HLA region. From this, and given the recent onset of cystic acne in the proband FRA1-1, it is concluded that FRA and PAPA syndrome are likely the same disorder.

A further disorder has been described as "streaking leukocyte factor" (Jacobs and Goetzl, 1975, *Pediatrics* 56:570). The description of this disease appears very similar, if not identical to FRA and PAPA syndrome, as the patient described had a history of sterile pyarthrosis and cutaneous inflammation and ulceration since the second year of life, with no increased incidence of infections of any kind. Family history of the disorder, however, was not reported. Interestingly the authors reported partial purification of a serum factor (MW 160 kd) which enhanced the random migration of purified normal human neutrophils or mononuclear leukocytes but did not appear to affect chemotaxis.

There is still a need, however, to identify and isolate the specific gene or genes that are involved in familial recurrent arthritis (FRA) and related disorders in order to provide means of diagnosis and management of the disorders, and to provide insights into the pathogenesis of the autoimmune joint destruction that is symptomatic of these and other autoimmune inflammatory conditions.

SUMMARY

The present disclosure includes the identification of a gene encoding the CD2 binding protein, CD2BP1, as the inherited factor associated with familial recurrent arthritis. In addition, mutant alleles of CD2BP1 are identified as a causative factor in the disorder. The invention also includes isolated nucleic acid molecules that encode mutations in the gene encoding CD2BP1, and particularly isolated genes that encode an amino acid sequence comprising the sequence of SEQ ID NO:2, and a composition including a partially purified protein encoded by the nucleic acid molecules. The invention also includes isolated nucleic acid molecules that include the nucleic acid sequence of SEQ ID NO:1, including expression vectors and host cells transfected with such vectors.

The present disclosure also includes methods of diagnosing an immune disorder in a subject comprising detecting a mutation in a CD2BP1 gene allele in a subject, and methods of diagnosis familial recurrent arthritis comprising detecting a gene allele comprising the sequence of SEQ ID NO:1.

Another aspect of the present disclosure is methods of screening for agents that modify an immune response in cells, and in organisms in which certain cells express a CD2BP1 with a mutation including a E250Q mutation. As used herein, a term such as E250Q denotes a mutation in a protein sequence at the position of amino acid 250. The first letter is the one letter designation of the naturally occurring amino acid (glutamic acid, E) and the last letter is the one letter designation of the amino acid that is substituted (glutamine, Q). Such assays typically include contacting cells or tissues with an agent suspected of modifying an immune response, measuring an indicator of immune response, and comparing that measurement to the same immune response indicator in a control cell or tissue under comparable conditions in the absence of the agent. A difference in the measured response in comparison to the measured control is indicative of an agent that modifies an immune response. It is understood that an agent that modifies an immune response may inhibit or enhance the immune response.

Preferred cells for use in the described assays would include immune cells such as T-cells or NK cells for example, and would also include cells or tissues that include cells that express CD2 or even CD15 expressing cells, either naturally occurring cells, or cells that have been engineered to express recombinant CD2 or CD15.

One may use any immune response assay known in the art, and particularly assays known to involve CD2. Such assays would include, but are not limited to T-cell rosetting, calcium flux, Il-2 production and cytolytic activity.

Another aspect of the disclosure is methods of screening for an agent that modifies an interaction of CD2 with a mutant CD2BP1, preferably a CD2BP1 protein with a E250Q mutation. Binding assays may include determining the binding of the cytoplasmic portion of CD2 and the mutant CD2BP1 in the presence of an agent suspected of altering the binding interaction of CD2 and CD2BP1/E250Q, and comparing the binding in the presence of the agent to the binding interaction in the absence of the agent, wherein a difference in the binding interaction is indicative of an effector of CD2 binding to the mutant CD2BP1. Such assays may also be used to screen for agents that modify the interaction of a mutant CD2BP1 with PTP PEST (Li, et al., *EMBO* 17(24):7320–7336, 1998); the interaction with the human homolog of PTP HSCF (Spencer et al., *J. Cell. Biol.* 138(4):845–60 (1997); Dowbenko et al., *J. Biol. Chem.* 273(2):989–96, 1998); the interaction with the human homolog of the Wiskott-Aldrich Syndrome Protein (WASP) (Wu et al., *J. Biol. Chem.*, 273(10), 5765–5770 1998); or the interaction with the human homolog of CD66a (Warren et al., *J. Immunology*, 156: 2876–2873, 1996; Stocks and Kerr, *Biochem J.*, 288, 23–27, 1992; Stocks, et al., *Biochem J.* 268, 275–280, 1990; Kammerer et al, *Eur. J. Immunology*, 28(11):3664–3674, 1998); Lucka et al., *FEBS Letters*, 438:37–40, 1998).

Binding assays may be any known in the art and would include immunoprecipitation or Western blot assays with monoclonal antibodies to any of the binding partners, or an assay that ncludes a fusion of a protein such as CD2BP1 to an immunological marker such as GST. Other assays would include the yeast two hybrid assay as described in Li et al. (1998) (incorporated herein by reference).

BRIEF DESCRIPTION OF THE DRAWING

FIG. 1 is an alignment of the amino acid sequences of human CD2BP1 and murine PSTPIP. The amino acid sequence of CD2BP1 is designated herein as SEQ ID NO:1, the N terminal amino acid sequence of PSTPIP from 1–323 is designated herein as SEQ ID NO: 2 and the C terminal amino acid sequence of PSTPIP from 324–416 is designated herein as SEQ ID NO:3. Sequences exhibiting high homology to yeast cdc15 include the region from amino acid 122–288. The sequences with high homology to a typical SH3 domain are amino acids 360–417. The potential PEST regions are underlined.

DETAILED DESCRIPTION

The present invention arises from the discovery that CD2BP1, an adaptor protein mediating CD2 function in activated T cells, is mutated in FRA affected individuals. This finding identifies CD2BP1 as central to a biochemical pathway which, when altered, can trigger inappropriate immune or autoimmune responses. The discovery of this mutation also provides for methods of screening for the disorder for the purposes of diagnosis of the disease and genetic counseling. In addition, the mutated protein may be used for high throughput assays to discover complementary mutations in the biochemical pathway, and/or for the discovery of therapeutic agents useful for the treatment or management of FRA or other immune disorders.

An aspect of the present invention is the binding interaction of the mutant CD2BP1 to the known interactors, PTP PEST, (protein tyrosine phosphatase, proline-glutamate-serine-threonine rich region) and CD2, the levels of phosphorylation of the mutant protein, and the effects of the binding and phosphorylation state on the pathology of immune disorders. In addition, an aspect of the present invention is the binding interaction of the mutant CD2BP1 with interactors identified in the murine system, PTP HSCF, and WASP. Another aspect of the present invention is the potential binding interaction of the mutant CD2BP1 and (human) CD 15 carriers, in particular, CD66a. In the murine system, the murine homolog of CD2BP1, proline, serine, threonine phosphatase interacting protein (PSTPIP) has been demonstrated to bind to another protein tyrosine phosphatase, PTP HSCF (protein tyrosine phosphatase hematopoietic stem cell fraction). This can be achieved with a portion of the PTP HSCF protein containing amino acids 1–264. A W232A mutation of PSTPIP results in complete loss of binding to PTP HSCF in vitro, as well as loss of association of the two proteins in co-transfected COS cells. Little or no change in binding activity was seen in alanine scanning mutants of various positions throughout the N-terminal coiled-coil domain of PSTPIP, suggesting that the region critical for PTP HSCF binding is within amino acids 232–264 of the PSTPIP protein (Dowbenko et al., 1998, Journal of Biological Chemistry 273:989), which would include (in the homolog) the amino acid reported herein to be associated with FRA (E250Q). The murine homolog PSTPIP also has been demonstrated to interact through its SH3 domain with the murine homolog of the Wiskott Aldrich Syndrome Protein (WASP), an event which appears to be regulated by tyrosine phosphorylation of PSTPIP. CD15 carriers are potential interactors with CD2BP1; CD15 levels measured on neutrophils of FRA patients are approximately 10–15% of normal. In the previous case report of what was described as "streaking leukocyte factor" (Jacobs and Goetzl, 1975, Pediatrics 56:570), the authors reported partial purification of a serum factor (MW 160 kd) which enhanced the random migration of purified normal human neutrophils or mononuclear leukocytes but did not appear to affect chemotaxis. This protein may be the potential CD2BP1 interactor CD66a, the major carrier of CD 15 on neutrophils.

The E250Q mutation could alter the binding of human PTP HSCF, subsequently changing the degree of phosphorylation of the CD2BP1 protein. Alternatively this mutation may alter interaction with an as yet unidentified protein that is expressed in a cell-specific manner. This is a plausible scenario given that the E250Q mutation results in a recurring autoimmune inflammation limited to a few physiological sites, rather than a global compromise of immune function.

The present disclosure therefore, encompasses:
(a) DNA vectors that contain a mutant CD2BP1 encoding sequence as described herein and/or their complements (i.e., antisense);
(b) DNA expression vectors that contain any of the foregoing mutant CD2BP1 coding sequences operatively associated with a regulatory element that directs the expression of the coding sequences; and (c) genetically engineered host cells that contain any of the foregoing mutant CD2BP1 coding sequences operatively associated with a regulatory element that directs the expression of the coding sequences in the host cell.

As used herein, regulatory elements include but are not limited to inducible and non-inducible promoters, enhancers, operators and other elements known to those skilled in the art that drive and regulate expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast alpha-mating factors.

The invention further includes fragments of any of the DNA sequences disclosed herein, in particular those fragments that include the coding region of amino acid 250 of the CD2BP1 gene and more particularly those that include a missense mutation at amino acid 250, and even more particularly those that include a G to C transversion at nucleotide 748 as numbered in SEQ ID NO:18. In one embodiment, the CD2BP1 gene sequences of the invention are human gene sequences, with homologous mammalian gene sequences with the analogous mutations also being included, in particular a sequence encoding a mutation at amino acid 250 in the murine PSTPIP protein.

In the practice of the present invention, mutant CD2BP1 gene products, or peptide fragments thereof, can be prepared for a variety of uses. For example, such gene products, or peptide fragments thereof, can be used for the generation of antibodies, in diagnostic assays, or for the identification of other cellular or extracellular gene products involved in the regulation of a CD2BP1 mediated disorder, such as FRA. The amino acid sequence of SEQ ID NO:2 represents a mutant CD2BP1 gene product. The CD2BP1 gene product, sometimes referred to herein as a "mutant CD2BP1 protein", includes those gene products encoded by the CD2BP1 gene sequences described above. In addition, CD2BP1 gene products may include proteins that represent functionally equivalent gene products. Such an equivalent CD2BP1 gene product may also contain deletions, including internal deletions, additions, including additions yielding fusion proteins, or substitutions of amino acid residues within and/or adjacent to the amino acid sequence encoded by the CD2BP1 gene sequences described, above, but that result in a "silent" change, in that the change produces a functionally equivalent mutant CD2BP1 gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged basic) amino acids include arginine, lysine, and histidine; and negatively charged (acidic) amino acids include aspartic acid and glutamic acid.

Alternatively, where alteration of function is desired, deletions or non-conservative halterations can be engineered to produce altered CD2BP1 gene products. Such alterations can, for example, include the substitution of other amino acids at position 250 in the CD2BP1, protein, or the deletion or substitution of amino acids in the region of the protein involved in binding to PTP PEST, WASP, PTP HSCF, CD15 carriers, or CD2, such as amino acids 232–264 or the SH3 region, amino acids 360–417 of CD2BP1. Alterations in the CD2BP1 protein may therefore be chosen to affect binding to the known or unknown cytoplasmic interactors as well as to soluble factors, ligands, or cell surface proteins or markers that interact with CD2 or CD2BP1 at the cell surface.

The CD2BP1 gene products, peptide fragments thereof and fusion proteins thereof, may be produced by recombinant DNA technology using techniques well known in the art. Thus, methods for preparing the CD2BP1 gene polypeptides, peptides, fusion peptide and fusion polypeptides of the invention by expressing nucleic acid containing CD2BP1 gene sequences are described herein. Methods that are well known t o those skilled in the art can be used to construct expression vectors containing CD2BP1 gene product coding sequences and appropriate transcriptional and translational control signals. These methods include, for example, in vitro recombinant DNA techniques, synthetic techniques, and in vivo genetic recombination. See, for example, the techniques described in Sambrook, et al., 1989, Molecular Cloning, A Laboratory Manual, Second Edition, Cold Spring Harbor Press, N.Y.; and Ausubel, et al., eds., 1989, Current Protocols in Molecular Biology, vol. I, Green Publishing Associates, Inc., and John Wiley & Sons, Inc., N.Y., at p. 2.10.3. Alternatively, RNA capable of encoding CD2BP1 gene product sequences may be chemically synthesized using, for example, synthesizers. See, for example, the techniques described in "Oligonucleotide Synthesis", 1984, Gait, ed., IRL Press, Oxford.

A variety of host-expression vector systems may be utilized to express the CD2BP1 gene coding sequences of the invention. Such host-expression systems represent vehicles by which the coding sequences of interest may be produced and subsequently purified, but also represent cells that may, when transformed or transfected with the appropriate nucleotide coding sequences, exhibit the CD2BP1 gene product of the invention in situ. These include but are not limited to microorganisms such as bacteria (e.g., E. coli, B. subtilis) transformed with recombinant bacteriophage DNA, plasmid DNA or cosmid DNA expression vectors containing CD2BP1 gene product coding sequences; yeast (e.g., Saccharomyces, Pichia) transformed with recombinant yeast expression vectors containing the CD2BP1 gene product coding sequences; insect cell systems infected with recombinant virus expression vectors (e.g., baculovirus) containing the CD2BP1 gene product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing CD2BP1 gene product coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter, CMV promoter).

In bacterial systems, a number of expression vectors may be advantageously selected depending upon the use intended for the CD2BP1 gene product being expressed. For example, when a large quantity of such a protein is to be produced, for the generation of highly purified compositions of CD2BP1 protein or for raising antibodies to CD2BP1 protein, for example, vectors that direct the expression of high levels of fusion protein products that are readily purified may be desirable. Such vectors include, but are not limited, to the *E. coli* expression vector pUR278 (Ruther et al., 1983, EMBO J. 2, 1791), in which the CD2BP1 gene product coding sequence may be ligated individually into the vector in frame with the lac Z coding region so that a fusion protein is produced; pIN vectors (Inouye and Inouye, 1985, Nucleic Acids Res. 13, 3101–3109; Van Heeke and Schuster, 1989, J. Biol. Chem. 264, 5503–5509); and the like. PGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, Autographa califomica, nuclear polyhedrosis virus (AcNPV) is used as a vector to express foreign genes. The virus grows in Spodoptera frugiperda cells. The CD2BP1 gene coding sequence may be cloned individually into non-essential regions (for example the polyhedrin gene) of the virus and placed under control of an ACNPV promoter (for example the polyhedrin promoter). Successful insertion of CD2BP1 gene coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed. (e.g., see Smith, et al., 1983, J. Virol. 46, 584; Smith, U.S. Pat. No. 4,215,051).

In mammalian host cells, a number of viral-based expression systems may be utilized. In cases where an adenovirus is used as an expression vector, the CD2BP1 gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing CD2BP1 gene product in infected hosts. (e.g., See Logan and Shenk, 1984, Proc. Natl. Acad. Sci. USA 81, 3655–3659). Specific initiation signals may also be required for efficient translation of inserted CD2BP1 gene product coding sequences. These signals include the ATG initiation codon and adjacent sequences. In cases where an entire CD2BP1 gene, including its own initiation codon and adjacent sequences, is inserted into the appropriate expression vector, no additional translational control signals may be needed. However, in cases where only a portion of the CD2BP1 gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner, et al., 1987, Methods in Enzymol. 153, 516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, and WI38.

For long-term, high-yield production of recombinant proteins, stable expression is preferred. For example, cell lines that stably express the CD2BP1 gene product may be engineered. Rather than using expression vectors that contain viral origins of replication, host cells can be transformed with DNA controlled by appropriate expression control elements (e.g., promoter, enhancer, sequences, transcription termninators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method may advantageously be used to engineer cell lines that express the CD2BP1 gene product. Such engineered cell lines may be particularly useful in screening and evaluation of compounds that affect the endogenous activity of the CD2BP1 gene product.

A number of selection systems may be used, including but not limited to the herpes simplex virus thymidine kinase (Wigler, et al., 1977, Cell 11,223), hypoxanthine-guanine phosphoribosyltransferase (Szybalska and Szybalski, 1962, Proc. Natl. Acad. Sci. USA 48, 2026), and adenine phosphoribosyltransferase (Lowy, et al., 1980, Cell 22, 817) genes can be employed in tk-, hgprt- or aprt-cells, respectively. Also, antimetabolite resistance can be used as the basis of selection for the following genes: dhfr, which confers resistance to methotrexate (Wigler, et al., 1980, Natl. Acad. Sci. USA 77, 3567; O'Hare, et al., 1981, Proc. Natl. Acad. Sci. USA 78, 1527); gpt, which confers resistance to mycophenolic acid (Mulligan and Berg, 1981, Proc. Natl. Acad. Sci. USA 78, 2072); neo, which confers resistance to the aminoglycoside G-418 (Colberre-Garapin, et al., 1981, J. Mol. Biol. 150, 1); and hygro, which confers resistance to hygromycin (Santerre, et al., 1984, Gene 30, 147).

Alternatively, any fusion protein may be readily purified by utilizing an antibody or ligand specific for the fusion protein being expressed. For example, a system described by Janknecht, et al. allows for the ready purification of non-denatured fusion proteins expressed in human cell lines (Janknecht, et al., 1991, Proc. Natl. Acad. Sci. USA 88, 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers. HIS-tagged fusion proteins may be produced from plasmid vectors as well.

The CD2BP1 gene products can also be expressed in transgenic animals. Animals of any species, including, but not limited to, mice, rats, rabbits, guinea pigs, pigs, micropigs, goats, sheep, and non-human primates, e.g., baboons, monkeys, and chimpanzees may be used to generate CD2BP1 transgenic animals. The term "transgenic," as used herein, refers to animals expressing CD2BP1 gene sequences from a different species (e.g., mice expressing human CD2BP1 sequences), as well as animals that have been genetically engineered to overexpress endogenous (i.e., same species) CD2BP1 sequences or animals that have been genetically engineered to no longer express endogenous CD2BP1 gene sequences (i.e., "knock-out" animals), and their progeny. Transgenic expression of mutant CD2BP1 proteins as described herein provides, for example, an important animal model for the study of immune disorders including FRA.

Any technique known in the art may be used to introduce a mutant CD2BP1 gene transgene into animals to produce the founder lines of transgenic animals. Such techniques include, but are not limited to pronuclear microinjection (Hoppe and Wagner, 1989, U.S. Pat. No. 4,873,191); retrovirus mediated gene transfer into germ lines (Van der Putten, et al., 1985, Proc. Natl. Acad. Sci., USA 82, 6148–6152); gene targeting in embryonic stem cells (Thompson, et al., 1989, Cell 56, 313–321); electroporation of embryos (Lo, 1983, Mol. Cell. Biol. 3, 1803–1814); and sperm-mediated gene transfer (Lavitrano et al., 1989, Cell 57, 717–723) (For a review of such techniques, see Gordon, 1989, Transgenic Animals, Intl. Rev. Cytol. 115; 171–229).

Any technique known in the art may be used to produce transgenic animal clones containing an CD2BP1 transgene, for example, nuclear transfer into enucleated oocytes of nuclei from cultured embryonic, fetal or adult cells induced to quiescence (Campbell, et al., 1996, Nature 380, 64–66; Wilmut, et al., Nature 385, 810–813).

The present invention thus provides for transgenic animals that carry a mutant CD2BP1 transgene in all their cells, as well as animals that carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type, hematopoietic cells, for example, by following the teaching of Lasko et al. (Lasko, et al., 1992, Proc. Natl. Acad. Sci. USA 89, 6232–6236). The regulatory sequences required for such a cell-type specific activation will depend upon the particular cell type of interest, and will be apparent to those of skill in the art. When it is desired that the CD2BP1 gene transgene be integrated into the chromosomal site of the endogenous CD2BP1 gene, gene targeting is preferred. Briefly, when such a technique is to be utilized, vectors containing some nucleotide sequences homologous to the endogenous CD2BP1 gene are designed for the purpose of integrating, via homologous recombination with chromosomal sequences, into and disrupting the function of the nucleotide sequence of the endogenous CD2BP1 gene. The transgene may also be selectively introduced into a particular cell type, thus inactivating the endogenous CD2BP1 gene in only that cell type, by following, for example, the teaching of Gu, et al. (Gu, et al., 1994, Science 265, 103–106). The regulatory sequences required for such a cell-type specific inactivation will depend upon the particular cell type of interest, and will be apparent to those of skill in the art.

Once transgenic animals have been generated, the expression of the recombinant mutant CD2BP1 gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques that include but are not limited to Northern blot analysis of tissue samples obtained from the animal, in situ hybridization analysis, and RT-PCR (reverse transcriptase PCR). Samples of CD2BP1 gene-expressing tissue, may also be evaluated immunocytochemically or by other in vitro techniques such as Western Blotting using antibodies specific for the CD2BP1 transgene product.

Also described herein are methods for the production of antibodies capable of specifically recognizing one or more mutant CD2BP1 gene product epitopes or epitopes of conserved variants or peptide fragments of the CD2BP1 gene products. Because a most useful antibody would be one that could distinguish the mutant CD2BP1 protein from the wild type, monoclonal antibodies are preferred. Such antibodies may be used, for example, in the detection of a CD2BP1 gene product in a biological sample and may, therefore, be utilized as part of a diagnostic or prognostic technique whereby patients may be tested for abnormal CD2BP1 gene products. Such antibodies may also be utilized in conjunction with, for example, compound screening schemes for the evaluation of the effect of test compounds on CD2BP1 gene product activity.

For the production of antibodies against a CD2BP1 gene product, various host animals may be immunized by injection with a mutant CD2BP1 gene product, or a portion thereof. Such host animals may include, but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and Corynebacterium parvum.

Monoclonal antibodies, which are homogeneous populations of antibodies to a particular antigen, may be obtained by any technique that provides for the production of antibody molecules by continuous cell lines in culture. These include, but are not limited to, the hybridoma technique of Kohler and Milstein, (1975, Nature 256, 495–497; and U.S. Pat. No. 4,376,110), the human B-cell hybridoma technique (Kosbor et al., 1983, Immunology Today 4, 72; Cole et al., 1983, Proc. Natl. Acad. Sci. USA 80, 2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison, et al., 1984, Proc. Natl. Acad. Sci., 81, 6851–6855; Neuberger, et al., 1984, Nature 312, 604–608; Takeda, et al., 1985, Nature, 314, 452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.)

Techniques have also been developed for the production of humanized antibodies. (See, e.g., Queen, U.S. Pat. No. 5,585,089, which is incorporated herein by reference in its entirety.) An immunoglobuin light or heavy chain variable region consists of a "framework" region interrupted by three hypervariable regions, referred to as complementarity determining regions (CDRs). The extent of the framework region and CDRs have been precisely defined (see, "Sequences of Proteins of Immunological Interest", Kabat, E. et al., U.S. Department of Health and Human Services (1983). Briefly, humanized antibodies are antibody molecules from non-human species having one or more CDRs from the non-human species and a framework region from a human immunoglobulin molecule. Alternatively, techniques described for the production of single chain antibodies (U.S. Pat. No. 4,946,778; Bird, 1988, Science 242, 423–426; Huston, et al., 1988, Proc. Natl. Acad. Sci. USA 85, 5879–5883; and Ward, et al., 1989, Nature 334, 544–546) can be adapted to produce single chain antibodies against CD2BP1 gene products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the F(ab')2 fragments, which can be produced by pepsin digestion of the antibody molecule and the Fab fragments, which can be generated by reducing the disulfide bridges of the F(ab')2 fragments. Alternatively, Fab expression libraries may be constructed (Huse, et al.,1989, Science, 246, 1275–1281) to allow rapid and easy identification of monoclonal Fab fragments with the desired specificity.

An aspect of the present disclosure is also various applications of CD2BP1 gene sequences, CD2BP1 gene products, including peptide fragments and fusion proteins thereof, and of antibodies directed against CD2BP1 gene products and peptide fragments thereof. Such applications include, for example, prognostic and diagnostic evaluation of a CD2BP1 mediated immune disorder such as FRA, and the identification of subjects with a predisposition to such disorders. Additionally, such applications include methods for the identification of compounds that modulate the expression of the CD2BP1 gene and/or the synthesis or activity of the CD2BP1 gene product. Such compounds can include, for example, other cellular products that are involved in the immune response signaling processes.

A variety of methods can be employed to screen for the presence of CD2BP1 mutations, and in particular the FRA associated mutation described herein. Nucleic acid from any nucleated cell can be used as the starting point for such assay techniques, and may be isolated according to standard nucleic acid preparation procedures that are well known to those of skill in the art. CD2BP1 nucleic acid sequences may be used in hybridization or amplification assays of biological samples to detect the described mutation in the CD2BP1 gene structure. Such assays may include, but are not limited to, denaturing HPLC, Southern analyses, single-stranded conformational polymorphism analyses (SSCP), DNA sequencing and PCR analyses. Diagnostic methods for the detection of the mutant CD2BP1 gene, in patient samples or other appropriate cell sources, may thus involve their amplification, e.g., by PCR (the experimental embodiment set forth in Mullis, 1987, U.S. Pat. No. 4,683,202), followed by the detection and/or nucleotide sequencing of the amplified molecules using standard techniques.

An aspect of the invention is also assays designed to identify compounds that bind to a mutant CD2BP1 gene product and intracellular proteins or portions of proteins that interact with a mutant CD2BP1 gene product. Such intracellular proteins or portions of proteins may be involved in the control and/or regulation of an immune response.

Compounds that may be so identified may include, but are not limited to, peptides such as, for example, soluble peptides, including but not limited to, Ig-tailed fusion peptides, and members of random peptide libraries; (see, e.g., Lam, et al., 1991, Nature 354, 82–84; Houghten, et al., 1991, Nature 354, 84–86), and combinatorial chemistry-derived molecular library made of D- and/or L-configuration amino acids, phosphopeptides (including, but not limited to members of random or partially degenerate, directed phosphopeptide libraries; see, e.g., Songyang, et al., 1993, Cell 72, 767–778), antibodies (including, but not limited to, polyclonal, monoclonal, humanized, anti-idiotypic, chimeric or single chain antibodies, and FAb, F(ab')2 and FAb expression library fragments, and epitope-binding fragments thereof), antisense RNA, ribozymes, and small organic or inorganic molecules. Such compounds may further comprise compounds, in particular drugs or members of classes or families of drugs, known to ameliorate or exacerbate the symptoms of an immune disorder such as FRA by acting on the cellular immune response signaling pathways. Compounds identified via assays such as those described herein may be useful, for example, in compensating for the mutation in CD2BP1 in the treatment or management of immune disorders such as FRA.

In vitro systems may be designed to identify compounds capable of binding the mutant CD2BP1 gene products of the invention. The principle of the assays used to identify compounds that bind to the mutant CD2BP1 gene product involves preparing a reaction mixture of the CD2BP1 gene product and the test compound under conditions and for a time sufficient to allow the two components to interact and bind, thus forming a complex that can be removed and/or detected in the reaction mixture. These assays can be conducted in a variety of ways. For example, one method to conduct such an assay would involve anchoring CD2BP1 gene product or the test substance onto a solid phase and detecting CD2BP1 gene product/test compound complexes anchored on the solid phase at the end of the reaction. In one embodiment of such a method, the CD2BP1 gene product may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the previously non-immobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for CD2BP1 gene product or the test compound to anchor any complexes formed in solution, and a labeled antibody specific for the other component of the possible complex to detect anchored complexes.

Any method suitable for detecting protein-protein interactions may be employed for identifying mutant CD2BP1 protein-protein interactions to identify intracellular binding partners. Among the traditional methods that may be employed are co-immunoprecipitation, cross-linking and co-purification through gradients or chromatographic columns. Utilizing procedures such as these allows for the identification of proteins, including intracellular proteins, that interact with mutant CD2BP1 gene products. Once isolated, such a protein can be identified and can be used in conjunction with standard techniques, to identify proteins with which it interacts. For example, at least a portion of the amino acid sequence of a protein that interacts with the CD2BP1 gene product can be ascertained using techniques well known to those of skill in the art, such as via the Edman degradation technique (see, e.g., Creighton, 1983, "Proteins: Structures and Molecular Principles," W. H. Freeman & Co., N.Y., pp.34–49). The amino acid sequence obtained may be used as a guide for the generation of oligonucleotide mixtures that can be used to screen for gene sequences encoding such proteins. Screening made be accomplished, for example, by standard hybridization or PCR techniques. Techniques for the generation of oligonucleotide mixtures and the screening are well-known. (See, e.g., Ausubel, supra, and 1990, "PCR Protocols: A Guide to Methods and Applications," Innis, et al., eds. Academic Press, Inc., New York).

Additionally, methods may be employed that result in the simultaneous identification of genes that encode the a protein which interacts with an CD2BPl protein. These methods include, for example, probing expression libraries with labeled CD2BP1 protein, using CD2BP1 protein in a manner similar to the well known technique of antibody probing of lambda gtll libraries.

One method that detects protein interactions in vivo, the two-hybrid system, is described in detail for illustration only and not by way of limitation. One version of this system has been described (Chien, et al., 1991, Proc. Natl. Acad. Sci. USA, 88, 9578–9582) and is commercially available from Clontech (Palo Alto, Calif.). Briefly, utilizing such a system, plasmids are constructed that encode two hybrid proteins: one consists of the DNA-binding domain of a transcription activator protein fused to the CD2BP1 gene product and the other consists of the transcription activator protein's activation domain fused to an unknown protein that is encoded by a cDNA that has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, mutation containing CD2BP1 gene products may be used as the bait gene product. Total genomic or cDNA sequences are fused to the DNA encoding an activation domain. This library and a plasmid encoding a hybrid of a bait CD2BP1 gene product fused to the DNA-binding domain are co-transformed into a yeast reporter strain, and the resulting transformnants are screened for those that express the reporter gene. For example, and not by way of limitation, a bait CD2BP1 gene sequence, such as the open reading frame of the CD2BP1 gene, can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait CD2BP1 gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait CD2BP1 gene-GAL4 fusion plasmid into a yeast strain that contains a lacZ gene driven by a promoter that contains GAL4 activation sequence. A cDNA encoded protein, fused to GAL4 transcriptional activation domain, that interacts with bait CD2BP1 gene product will reconstitute an active GAL4 protein and thereby drive expression of the HIS3 gene. Colonies that express HIS3 can be detected by their growth on petri dishes containing semi-solid agar based media lacking histidine. The cDNA can then be purified from these strains, and used to produce and isolate the bait CD2BP1 gene-interacting protein using techniques routinely practiced in the art.

CD2BP1 gene products of the invention may, in vivo, interact with one or more macromolecules, including intracellular macromolecules, such as proteins. Such macromolecules may include, but are not limited to, nucleic acid molecules and those proteins identified via methods such as those described above, as well as proteins known to interact with the wild-type CD2BP1 such as the cytoplasmic tail of CD2 or PTP PEST, for example. For purposes of this disclosure, the macromolecules are referred to herein as "binding partners". Compounds that disrupt mutant CD2BP1 binding in this way may be useful in regulating the activity of the CD2BP1 gene product, especially mutant CD2BP1 gene products. Such compounds may include, but are not limited to molecules such as peptides, and the like, which would be capable of gaining access to a CD2BP1 gene product.

The basic principle of the assay systems used to identify compounds that interfere with the interaction between the CD2BP1 gene product and its binding partner or partners involves preparing a reaction mixture containing the CD2BP1 gene product, and the binding partner under conditions and for a time sufficient to allow the two to interact and bind, thus forming a complex. In order to test a compound for inhibitory activity, the reaction mixture is prepared in the presence and absence of the test compound.

The test compound may be initially included in the reaction mixture, or may be added at a time subsequent to the addition of CD2BP1 gene product and its binding partner. Control reaction mixtures are incubated without the test compound or with a placebo. The formation of any complexes between the CD2BP1 gene protein and the binding partner is then detected. The formation of a complex in the control reaction, but not in the reaction mixture containing the test compound, indicates that the compound interferes with the interaction of the CD2BP1 gene protein and the interactive binding partner. Additionally, complex formation within reaction mixtures containing the test compound and normal CD2BP1 gene protein may also be compared to complex formation within reaction mixtures containing the test compound and a mutant CD2BP1 gene protein. This comparison may be important in those cases wherein it is desirable to identify compounds that disrupt interactions of mutant but not normal CD2BP1 gene proteins.

The assay for compounds that interfere with the interaction of the CD2BP1 gene products and binding partners can be conducted in a heterogeneous or homogeneous format. Heterogeneous assays involve anchoring either the CD2BP1 gene product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the CD2BP1 gene products and the binding partners, e.g., by competition, can be identified by conducting the reaction in the presence of the test substance; i.e., by adding the test substance to the reaction mixture prior to or simultaneously with the CD2BP1 gene protein and interactive intracellular binding partner. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the CD2BP1 gene product or the interactive binding partner, is anchored onto a solid surface, while the non-anchored species is labeled, either directly or indirectly. In.practice, microtiter plates are conveniently utilized. The anchored species may be immobilized by non-covalent or covalent attachments. Non-covalent attachment may be accomplished simply by coating the solid surface with a solution of the CD2BP1 gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. In this approach, a preformed complex of the mutant CD2BP1 gene protein and the interactive binding partner is prepared in which either the CD2BP1 gene product or its binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances that disrupt CD2BP1 gene protein/binding partner interaction can be identified.

In a particular embodiment, the mutant CD2BP1 gene product can be prepared for immobilization using recombinant DNA techniques. For example, the CD2BP1 coding region can be fused to a glutathione-S-transferase (GST) gene using a fusion vector, such as pGEX-5X-1, in such a manner that its binding activity is maintained in the resulting fusion protein. The interactive binding partner can be purified and used to raise a monoclonal antibody, using methods routinely practiced in the art. This antibody can be labeled with the radioactive isotope $^{125}$I, for example, by methods routinely practiced in the art. In a heterogeneous assay, e.g., the GST-CD2BP1 fusion protein can be anchored to glutathione-agarose beads. The interactive binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the CD2BP1 gene protein and the interactive binding partner can be detected by measuring the amount of radioactivity that remains associated with the glutathione-agarose beads. A successful inhibition of the interaction by the test compound will result in a decrease in measured radioactivity.

Alternatively, the GST-CD2BP1 gene fusion protein and the interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the CD2BP1 gene productibinding partner interaction can be detected by adding the labeled antibody and measuring the radioactivity associated with the beads.

In another embodiment of the invention, these same techniques can be employed using peptide fragments that correspond to the binding domains of the CD2BP1 protein and/or the interactive or binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the segments can be engineered to express peptide fragments of the protein, which can then be tested for binding activity and purified or synthesized. For example, and not by way of limitation, a mutant CD2BP1 gene product can be anchored to a solid material as described by making a GST-CD2BP1 fusion protein and allowing it to bind to glutathione agarose beads. The interactive binding partner obtained can be labeled with a radioactive isotope, such as $^{35}$S, and cleaved with a proteolytic enzyme such as trypsin. Cleavage products can then be added to the anchored GST-CD2BP1 fusion protein and allowed to bind. After washing away unbound peptides, labeled bound material, representing the binding partner binding domain, can be eluted, purified, and analyzed for amino acid sequence by well-known methods. Peptides so identified can be produced synthetically or fused to appropriate facilitative proteins using recombinant DNA technology.

In a further aspect of the invention, animal-based systems or models for a CD2BP1 mediated immune disorder, which may include, for example, mutant CD2BP1 or mutant PST-PIP expressing mice, may be used to identify compounds capable of ameliorating symptoms of the disorder. Such animal models may be used as test substrates for the identification of drugs, pharmaceuticals, therapies and interventions that may be effective in treating such disorders. For example, animal models may be exposed to a compound suspected of exhibiting an ability to ameliorate symptoms, at a sufficient concentration and for a sufficient time to elicit such an amelioration of symptoms of an immune disorder in the exposed animals. The response of the animals to the exposure may be monitored by assessing the reversal of such symptoms. With regard to intervention, any treatments that reverse any aspect of symptoms of an immune disorder should be considered as candidates for human therapeutic intervention in such a disorder. Dosages of test agents may be determined by deriving dose-response curves.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

The following example describes the identification of the chromosomal region that harbors the causative gene for familial recurrent arthritis (FRA) via a genome wide linkage scan in an extended kindred with the disease. A genome wide linkage survey of this extended kindred localizes the causative gene to human chromosome 15q22–24.

A three generation family was ascertained in which nine members were diagnosed with juvenile idiopathic arthritis. In this family the disease was of very early onset and included episodic inflammation leading to eventual destruction of joints, muscle, and skin. The simple inheritance pattern and number of affected individuals in this family permitted the performance of a genome-wide linkage scan to localize the causative allele. This allele was contemplated to likely play a fundamental role in the immune cascade leading to tissue destruction in this disorder.

The proband, FRA1-1, presented as a 5-year-old boy with a history of recurrent joint swelling and cystic skin lesions since infancy. Arthritis was characteristically intermittent and migratory and led to the accumulation of sterile pyogenic material within the joint space if left untreated. It followed a mono-articular pattern (rarely more than one joint affected during flares). It involved primarily the elbows, knees, and ankles, although small joints were occasionally affected. There was no history of recurrent infections or granuloma formation. Family history was remarkable for the presence of similar symptoms in the patient's father and twin brothers, paternal aunt and two cousins. The father reported a marked improvement in joint symptoms after puberty, with the subsequent appearance of severe acne.

The proband's initial physical examination revealed a slightly pale boy in the 25th percentile for weight and 5th percentile for height. In general the examination was unremarkable except for the presence of 2×2 cm scar on the antero-lateral aspect of the right shoulder and a 50% loss of function of the left elbow, which displayed a 2×3 cm scar from a previous synovectomy. At the time of this initial visit, he was on low dose daily prednisone (5 mg) and nonsteroidal anti-inflammnatory drugs (NSAIDs). During the next four years, this patient continued presenting intermittent episodes of arthritis initially characterized by tenderness, erythema, and non-fluctuating joint swelling. These episodes either responded to the administration of intra-articular steroids, or evolved in a matter of days into a fluctuating stage with the accumulation of pseudo-purulent, sterile material that required surgical draining for healing to occur. During these episodes the patient remained afebrile, and laboratory tests characteristically showed anemia, normal white blood cell (WBC) count, and differential, elevated aldolase and erythrocyte sedimentation rate (ESR). Laboratory values typically returned to normal levels in between the arthritis episodes, except for aldolase, which remained elevated.

Cultures of the synovial fluid and tissue for bacteria, mycobacteria and fungi were repeatedly negative. Antinuclear antibodies (ANA), rheumatoid factor (RF), CH$_{50}$, C3, C4, and immunoglobulin levels were normal. Peripheral blood T, B, NK and monocyte cell counts as well as T and B cell subpopulations were normal according to flow cytometry markers (CD3, CD4, CD8, CD14, CD16, CD19, CD20, CD56). Nitroblue tetrazolium (NBT) and bactericidal capacity were normal. Synovial tissue biopsy revealed polymorphonuclear infiltrate, and immunofluorescence analysis failed to disclose the presence of immunoglobulin or complement deposits. At the age of eight, the patient began presenting erythematous/violaceous papular cutaneous lesions on the legs and arms that would evolve into sterile pustules and eventually into ulcers. This patient continued presenting recurrent attacks of joint and skin inflammation in spite of treatment with daily PO prednisone and intermittent intra-articular and high dose intravenous steroids. Trials of subcutaneous methotrexate, and PO hydroxychloroquine were unsuccessful. Surgical debridement of involved joints, specially the elbows, was required on several occasions in order to control the inflammatory process. At the time of this disclosure, this patient had normal joint function with the exception of a 25% and a 50% reduction in right and left elbow mobility respectively.

Two twin male siblings of the proband had a similar although milder clinical history. They also had recurrent joint swelling since infancy. As in the proband, swelling primarily involved single joints including the elbows, knees and ankles; however, no skin lesions compatible with pyoderma gangrenosum were noted. Laboratory results showed leukocytosis and elevated ESR during flares. Anemia was mild, and aldolase remained persistently elevated. These patients were treated with oral prednisone, and periodic local steroid injections to control their symptoms.

DNA was isolated from 10 mL whole blood by a differential lysis procedure (Boehringer Mannheim catalog no. 1667327). Fluorescently-labelled microsatellite markers were amplified with the polymerase chain reaction (PCR) in a Perkin-Elmer 9600 or M3 Research Tetrad thermocycler. Reactions were performed in 15 µL containing 1.5 mM $MgCl_2$, 500 mM KCl, 0.25 mM each dNTP, 1.25 pmol each primer, 0.5 U Taq polymerase (Perkin Elmer Cetus), and 100 ng patient DNA. Amplification conditions were 95° C. 5 minutes, then 28 cycles, 94° C. 30s, 56° C. 30s with a final extension of 6 minutes, 72° C. PCR products from each individual were pooled, mixed with loading dye and TAMRA 500 size standards (Perkin Elmer Cetus) and denatured for 5 minutes, 95° C. Alleles were separated by electrophoresis in a 12 or 36 cm 4.65% denaturing acrylamide gel at 760V for 2–3 hours with an ABI PRISM 377 DNA Sequencer/Genotyper (Applied Biosystems). Results were analyzed by the GeneScan (version 2.01) and GENOTYPER software packages (Applied Biosystems).

All alleles called by GENOTYPER were examined independently by two individuals. Uninformative markers were replaced with informative ones wherever possible. Two point lod scores were calculated by FASTLINK and MLINK versions of the LINKAGE program (Lathrop et al., 1984, *Proc Natl Acad Sci USA* 81:3443). Given that FRA is clearly a rare disorder, but of unknown prevalence, linkage calculations were performed incorporating gene frequencies of both 0.0001 and 0.00001. When available allele frequencies were obtained from the Marshfield Database (Marshfield Clinnc Center for Medicac Genetics, Marshfield, Wis.; for all other loci equal allele frequencies were used.

Whole blood lymphocytes from the proband's affected father were found to be karyotypically normal. Localization of the susceptibility gene therefore required a genome-wide linkage scan. A two-stage genome wide scan was initiated in which 169 polymorphic autosomal loci at an average resolution of approximately 25 cM were first genotyped in twelve family members including eight affected individuals. Pairwise lod scores using a model of dominant inheritance with 100% penetrance provided strongest evidence for linkage at D15S655 and D15S175. In the second stage of the survey an additional 102 polymorphic autosomal loci were genotyped in the original family as well as a newly-ascertained affected cousin, FRA-16, to provide finer mapping of all regions of potential linkage. Significant evidence of linkage was obtained only at D15S175 ($Z_{max}$=3.23 at $0_{max}$=0.0010), and increasing the estimated gene frequency from 0.00001 to 0.0001 did not significantly alter this result. Refinement of this region with additional loci generated the two point lod scores. Although lod scores for all loci were also generated with penetrances of 80 and 90%, the highest lod scores were obtained using 100% penetrance. The maximum lod score was obtained with D15S211 ($Z_{max}$=3.27, $0_{max}$=0.0010). Critical recombinants in this family localized FRA to a region approximately 20 cM flanked proximally by D15S983 and distally by D15S127 on chromosome 15.

Example 2

The following example describes the isolation and identification of a mutant allele in the gene encoding the CD2 binding protein, CD2BP1. The nucleic acid sequence of CD2BP1, long form is available as Genbank accession #AF038603. The mutation at nucleic acid 748 in the sequence described herein as SEQ ID NO:18 is shown herein to be associated with familial recurrent arthritis. The amino acid sequence of the E250Q mutant is designated herein as SEQ ID NO:19.

A partial physical and transcription map of the FRA critical region was constructed in silico by assembling BAC clones and known genes from public databases. BAC sequences found in Genbank were analysed for coding regions by the NIX gene prediction software suite (Human Genome Mapping Protocol (HGMP) Website), generating precise linear placement of several genes. Other genes were integrated from the G3 and GB4 radiation hybrid maps (NCBI Website). Arthritis and ulcerative skin lesions found in individuals affected with FRA appear to have an autoimmune aetiology; therefore priority was given to positional candidate genes expressed in hematopoietic tissues and/or those that were known to function in the inflammatory response. These genes were analyzed for mutations in affected individuals from family FRAI by either direct DNA sequencing or denaturing high performance liquid chromatography (DHPLC) to detect heteroduplex formation. Several genes were excluded by these analyses.

The CD2 binding protein 1 (CD2BP1) gene was considered a candidate for mutation screening for several reasons. It was originally identified by a yeast two-hybrid interaction trap system designed to detect proteins interacting with the cytoplasmic tail of the CD2 protein. CD2 is found on the surface of virtually all T cells and natural killer (NK) cells, where it mediates adhesion to target cells and antigen presenting cells (APCs). CD2BP1 expression is restricted almost exclusively to hematopoietic tissues as detected by Northern analysis, and evidence suggests that the CD2BP1 protein may function as a negative regulator of CD2 adhesion. In addition, the mouse homolog of CD2BP1, PSTPIP, has been demonstrated by the yeast two-hybrid system to interact with the protein which is deficient in Wiskott-Aldrich syndrome, an X-linked disorder marked by a compromised immune deficiency.

PCR primers were designed from the CD2BP1 cDNA sequence to amplify the cDNA in six overlapping fragments. These amplimers were generated by RT-PCR of total RNA from affected family members FRA1-1 and FRA1-10 EBV lymphoblastoid cell lines. Analysis by DHPLC detected heteroduplex formation in one amplified fragment, suggesting the presence of a sequence variant in one allele. Interestingly, alternative splicing of this region in activated T cells has been reported to generate two transcripts differing by 57 nucleotides (Li et al. *EMBO* 17(24):7320–7336 (1998)). However, only the longer version was detected in amplified patient or control lymphoblastoid cDNA. The same analysis of a portion of this fragment amplified from patient cDNA again detected a potential sequence variant. The exon/intron boundaries of CD2BP1 were derived by alignment of the cDNA sequence with human genomic sequence from the Celera database. This analysis indicated that the CD2BP1 gene contains 15 exons, with the alternatively spliced region encompassing exon 12. An intronic primer upstream of exon 11 was designed to amplify the variant-containing region from genomic DNA of FRA family members. DHPLC analysis of this 189 base pair amplimer, designated as 5' exon 11 demonstrated that the variant co-segregates with disease in the FRA family. Sequence analysis identified a G-to-C transversion at nucleotide 748 of the CD2BP1 cDNA. Sequencing of the cloned 5' exon 11 amplimer from affected individual FRA1-1 revealed 34% of clones with the G-to-C mutation and 66% wild type. DHPLC analysis of the 5' exon 11 amplimer of 228 control chromosomes from a panel of unrelated Caucasian Americans revealed no heterozygous sequence variants; 72 of these wild type chromosomes were confirmed by DNA sequencing. In addition, no heteroduplexes were detected by DHPLC analysis of controls mixed with wild type 5' exon 11 amplimer, suggesting the absence of any homozygous changes from the wild type sequence in this region in control individuals.

The mutant CD2BP1 nucleic acid sequence follows with the mutation at nucleotide 748 shown in bold:

1 atgatgcccc agctgcagtt caaagatgcc ttttggtgca gggacttcac agcccacacg
61 ggctacgagg tgctgctgca gcggcttctg gatggcagga agatgtgcaa agacatggag
121 gagctactga ggcagagggc ccaggcggag gagcggtacg ggaaggagct ggtgcagatc
181 gcacggaagg caggtggcca gacggagatc aactccctga gggcctcctt tgactccttg
241 aagcagcaaa tggagaatgt gggcagctca cacatccagc tggccctgac cctgcgtgag
301 gagctgcgga gtctcgagga gtttcgtgag aggcagaagg agcagaggaa gaagtatgag
361 gccgtcatgg accgggtcca gaagagcaag ctgtcgctct acaagaaggc catggagtcc
421 aagaagacat acgagcagaa gtgccgggac gcggacgacg cggagcaggc cttcgagcgc
481 attagcgcca acggccacca gaagcaggtg gagaagagtc agaacaaagc caggcagtgc
541 aaggactcgg ccaccgaggc agagcgggta tacaggcaga gcattgcgca gctggagaag
601 gtccgggctg agtgggagca ggagcaccgg accacctgtg aggcctttca gctgcaagag
661 tttgaccggc tgaccattct ccgcaacgcc ctgtgggtgc acagcaacca gctctccatg
721 cagtgtgtca aggatgatga gctctaccag gaagtgcggc tgacgctgga aggctgcagc
781 atagacgccg acatcgacag ttttcatccag gccaagagca cgggcacaga gcccccgct
841 ccggtgccct accagaacta ttacgatcgg gaggtcaccc cgctgaccag cagccctggc
901 atacagccgt cctgcggcat gataaagagg ttctctggac tgctgcacgg aagtcccaag
961 accacttcgt tggcagcttc tgctgcgtcc acagagaccc tgaccccccac ccccgagcgg
1021 aatgagggtg tctacacagc catcgcagtg caggagatac agggaaaccc ggcctcacca
1081 gcccaggagt accgggcgct ctacgattat acagcgcaga acccagatga gctggacctg
1141 tccgcgggag acatcctgga ggtgatcctg gaaggggagg atggctggtg gactgtggag
1201 aggaacgggc agcgtggctt cgtccctggt tcctacctgg agaagctttg aggaagggcc
1261 aggagcccct tcggacctgc cctgccagtg gagccagcag tgccccccag actgtcccca
1321 ccttgctagg gcccagaacc aagcgtcccc cagccccgag agggagcctg tcgtctccca
1381 gggaataaag gagtgcgttc tgttctaaaa aaaaaaaaaa aaaaaaaa, SEQ ID NO:18.

The predicted amino acid sequence of the CD2BP1 protein bears approximately 30% similarity to the *Schizosaccharomyces pombe* CDC15 protein, a phosphoprotein involved in organization of the actin ring and cleavage furrow formation during cytokinesis. The murine homolog PSTPIP has been demonstrated to co-localize with the cortical actin cytoskeleton, larnellipodia, and the cytokinetic cleavage furrow, and 3T3 cells in which the protein has been overexpressed form extended filopodia. In addition, overexpression of the PSTPIP protein in *S. pombe* inhibits cytokinesis. These observations led to the proposal that the murine homolog PSTPIP is functionally homologous to CDC15. Like CDC15, CD2BP1 contains a helical domain and a carboxy terminal SH3 region; in addition, a PEST sequence of variable length is found in the alternatively spliced sequence between these domains. The G748C missense mutation in CD2BP1 is predicted to change negatively charged glutamic acid (E) 250 to a polar uncharged glutamine (Q); this residue is conserved in both the murine protein PSTPIP, as well as within the *S. pombe* CDC 15 gene (FIG. 1). The G748C annotation denotes a G to C transversion at position 748 of the native sequence (Genbank Accession #AF038603), and the mutant sequence which is designated herein as SEQ ID NO:18.

METHODS

PCR amplification. Whole cell RNA was isolated from Epstein Barr virus-transformed lymphoblastoid cell lines established from patients FRA1-1 and FRA1-1 by a modified guanidium thiocyanate lysis procedure (Roche Boehringer Mannheim cat. number 1667 165). RNA was converted to cDNA by both random priming and dT priming with reverse transcriptase (Roche Boehringer Mannheim cat. number 1483 188). CD2BP1 was produced in six fragments by amplification of cDNA with the following primers: CD2BP1-1F: ATG ATG CCC CAG CTG CA, SEQ ID NO:4; CD2BP1-1R: CCT TCT GCC TCT CAC GAA AC, SEQ ID NO:5; CD2BP1-2F: CAA ATG GAG AAT G GGC AG, SEQ ID NO:6; CD2BP1-2R: TGG CTT TGT TCT GAC TCT TCT, SEQ ID NO:7; CD2BP1-3F: CCA AGA AGA CAT ACG AGC AGA AG, SEQ ID NO:8; CD2BP1-3R: CCG CAC TTC CTC GTA GAG, SEQ ID NO:9; CD2BP1-4F: GCA GTG TGT CAA GGA TGA TG, SEQ ID NO:10; CD2BP1-4R: GTC TCT GTG GAC GCA GCA G. SEQ ID NO:11; CD2BP1-5F: TGC CCT ACC AGA ACT ATT ACG, SEQ ID NO:12; CD2BP1-5R: CCA CAG TCC ACC AGC CAT, SEQ ID NO:13; CD2BP1-6F: CAG CGC AGA ACC CAG ATG A, SEQ ID NO:14; CD2BP1-6R: AGA ACA GAA CGC ACT CCT TT, SEQ ID NO:15.

The 5' exon 11 fragment was amplified from genomic DNA with CD2BP1 exon 11–109F: CAC AAT GGC CTG TGA GGA G, SEQ ID NO:16, and CD2BP1-1038R: CGT GCT CTT GGC CTG GAT, SEQ ID NO:17. All amplimers were generated in the polymerase chain reaction (PCR) in a Perkin-Elmer 9600 or MJ Research Tetrad thermocycler. Reactions were performed in 25 μl containing 1.5 mM MgCl$_2$, 500 mM KCl, 0.25 mM each dNTP, 1.0 pmol each primer, 0.5 U Taq polymerase (Perkin Elmer Cetus), and 100 ng patient DNA. Amplification conditions were 35 cycles, 94° C. 30s, 56° C. 30s, 72° C. 3s, except 5' exon 11 for which an annealing temperature of 55° C. was used.

Mutation analysis. Denaturing high performance liquid chromatography was performed with a WAVE machine (Transgenomics) utilizing conditions recommended by WaveMaker v3.3.3 software. CD2BP1 amplified fragments 1,2,3, and 5 were analyzed at an oven temperature of 65° C., fragments 4 and 5' exon 11 at 64° C., and fragment 6 at 66° C. For sequene products were purified from agarose gels with a purification kit (Qiagen). Amplimers were sequenced with the BigDye Terminator cycle sequencing ready reaction kit (Applied Biosystems). Sequencing products were separated by electrophoresis through a 36 cm 4.25% denaturing acrylamide gel at 760V for 3–7 hours with an ABI PRISM 377 DNA Sequencer/Genotyper (Applied Biosystems).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are chemically or physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An isolated nucleic acid molecule or the complement thereof, wherein said molecule encodes an amino acid sequence comprising the sequence of SEQ ID NO:19.

2. The molecule of claim 1, wherein said nucleic acid molecule comprises the nucleic acid sequence of SEQ ID NO:18.

3. An expression construct comprising the nucleic acid molecule of claim 1.

4. The expression construct of claim 3, further defined as a plasmid expression vector.

5. The expression construct of claim 3, further defined as a viral expression vector.

6. A host cell transformed or transfected with the expression construct of claim 3.

7. The host cell of claim 6, further defined as a bacterial cell.

8. The host cell of claim 6, further defined as a mammalian cell.

9. The host cell of claim 6, further defined as a human cell.

* * * * *

SEQUENCE LISTING

<160> NUMBER OF SEQ ID NOS: 19

<210> SEQ ID NO 1
<211> LENGTH: 416
<212> TYPE: PRT
<213> ORGANISM: Homo sapiens

<400> SEQUENCE: 1

```
Met Met Pro Gln Leu Gln Phe Lys Asp Ala Phe Trp Cys Arg Asp Phe
  1               5                  10                  15

Thr Ala His Thr Gly Tyr Glu Val Leu Leu Gln Arg Leu Leu Asp Gly
             20                  25                  30

Arg Lys Met Cys Lys Asp Met Glu Glu Leu Leu Arg Gln Arg Ala Gln
         35                  40                  45

Ala Glu Glu Arg Tyr Gly Lys Glu Leu Val Gln Ile Ala Arg Lys Ala
     50                  55                  60

Gly Gly Gln Thr Glu Ile Asn Ser Leu Arg Ala Ser Phe Asp Ser Leu
 65                  70                  75                  80

Lys Gln Gln Met Glu Asn Val Gly Ser Ser His Ile Gln Leu Ala Leu
                 85                  90                  95

Thr Leu Arg Glu Glu Leu Arg Ser Leu Glu Glu Phe Arg Glu Arg Gln
            100                 105                 110

Lys Glu Gln Arg Lys Lys Tyr Glu Ala Val Met Asp Arg Val Gln Lys
        115                 120                 125

Ser Lys Leu Ser Leu Tyr Lys Lys Ala Met Glu Ser Lys Lys Thr Tyr
    130                 135                 140

Glu Gln Lys Cys Arg Asp Ala Asp Ala Glu Gln Ala Phe Glu Arg
145                 150                 155                 160

Ile Ser Ala Asn Gly His Gln Lys Gln Val Glu Lys Ser Gln Asn Lys
                165                 170                 175

Ala Arg Gln Cys Lys Asp Ser Ala Thr Glu Ala Glu Arg Val Tyr Arg
            180                 185                 190

Gln Ser Ile Ala Gln Leu Glu Lys Val Arg Ala Glu Trp Gln Glu
        195                 200                 205

His Arg Thr Thr Cys Glu Ala Phe Gln Leu Gln Glu Phe Asp Arg Leu
    210                 215                 220

Thr Ile Leu Arg Asn Ala Leu Trp Val His Ser Asn Gln Leu Ser Met
225                 230                 235                 240

Gln Cys Val Lys Asp Asp Glu Leu Tyr Glu Glu Val Arg Leu Thr Leu
                245                 250                 255
```

```
Glu Gly Cys Ser Ile Asp Ala Asp Ile Asp Ser Phe Ile Gln Ala Lys
                260                 265                 270

Ser Thr Gly Thr Glu Pro Pro Ala Pro Val Pro Tyr Gln Asn Tyr Tyr
            275                 280                 285

Asp Arg Glu Val Thr Pro Leu Thr Ser Ser Pro Gly Ile Gln Pro Ser
        290                 295                 300

Cys Gly Met Ile Lys Arg Phe Ser Gly Leu Leu His Gly Ser Pro Lys
305                 310                 315                 320

Thr Thr Ser Leu Ala Ala Ser Ala Ser Thr Glu Thr Leu Thr Pro
                325                 330                 335

Thr Pro Glu Arg Asn Glu Gly Val Tyr Thr Ala Ile Ala Val Gln Glu
            340                 345                 350

Ile Gln Gly Asn Pro Ala Ser Pro Ala Gln Glu Tyr Arg Ala Leu Tyr
        355                 360                 365

Asp Tyr Thr Ala Gln Asn Pro Asp Glu Leu Asp Leu Ser Ala Gly Asp
    370                 375                 380

Ile Leu Glu Val Ile Leu Glu Gly Glu Asp Gly Trp Trp Thr Val Glu
385                 390                 395                 400

Arg Asn Gly Gln Arg Gly Phe Val Pro Gly Ser Tyr Leu Glu Lys Leu
                405                 410                 415

<210> SEQ ID NO 2
<211> LENGTH: 323
<212> TYPE: PRT
<213> ORGANISM: Mus musculus

<400> SEQUENCE: 2

Met Met Ala Gln Leu Gln Phe Arg Asp Ala Phe Trp Cys Arg Asp Phe
1               5                   10                  15

Thr Ala His Thr Gly Tyr Glu Val Leu Leu Gln Arg Leu Leu Asp Gly
            20                  25                  30

Arg Lys Met Cys Lys Asp Val Glu Glu Leu Leu Arg Gln Arg Ala Gln
        35                  40                  45

Ala Glu Glu Arg Tyr Gly Lys Glu Leu Val Gln Ile Ala Arg Lys Ala
    50                  55                  60

Gly Gly Gln Thr Glu Met Asn Ser Leu Arg Thr Ser Phe Asp Ser Leu
65                  70                  75                  80

Lys Gln Gln Thr Glu Asn Val Gly Ser Ala His Ile Gln Leu Ala Leu
                85                  90                  95

Ala Leu Arg Glu Glu Leu Arg Ser Leu Glu Glu Phe Arg Glu Arg Gln
            100                 105                 110

Lys Glu Gln Arg Lys Lys Tyr Glu Ala Ile Met Asp Arg Val Gln Lys
        115                 120                 125

Ser Lys Leu Ser Leu Tyr Lys Lys Thr Met Glu Ser Lys Lys Ala Tyr
    130                 135                 140

Asp Gln Lys Cys Arg Asp Ala Asp Ala Glu Gln Ala Phe Glu Arg
145                 150                 155                 160

Val Ser Ala Asn Gly His Gln Lys Gln Val Glu Lys Ser Gln Asn Lys
                165                 170                 175

Ala Lys Gln Cys Lys Glu Ser Ala Thr Glu Ala Glu Arg Val Tyr Arg
            180                 185                 190

Gln Asn Ile Glu Gln Leu Glu Arg Ala Arg Thr Glu Trp Glu Gln Glu
        195                 200                 205

His Arg Thr Thr Cys Glu Ala Phe Gln Leu Gln Glu Phe Asp Arg Leu
```

```
        210                 215                 220
Thr Ile Leu Arg Asn Ala Leu Trp Val His Cys Asn Gln Leu Ser Met
225                 230                 235                 240

Gln Cys Val Lys Asp Asp Glu Leu Tyr Glu Glu Val Arg Leu Thr Leu
                245                 250                 255

Glu Gly Cys Asp Val Glu Gly Asp Ile Asn Gly Phe Ile Gln Ser Lys
            260                 265                 270

Ser Thr Gly Arg Glu Pro Pro Ala Pro Val Pro Tyr Gln Asn Tyr Tyr
        275                 280                 285

Asp Arg Glu Val Thr Pro Leu Ile Gly Ser Pro Ser Ile Gln Pro Ser
        290                 295                 300

Cys Gly Val Ile Lys Arg Phe Ser Gly Leu Leu His Gly Ser Pro Lys
305                 310                 315                 320

Thr Thr Pro

<210> SEQ ID NO 3
<211> LENGTH: 92
<212> TYPE: PRT
<213> ORGANISM: Mus musculus

<400> SEQUENCE: 3

Ser Ala Pro Ala Ala Ser Thr Glu Thr Leu Thr Pro Thr Pro Glu Arg
  1               5                  10                  15

Asn Glu Leu Val Tyr Ala Ser Ile Glu Val Gln Ala Thr Gln Gly Asn
                 20                  25                  30

Leu Asn Ser Ser Ala Gln Asp Tyr Arg Ala Leu Tyr Asp Tyr Thr Ala
             35                  40                  45

Gln Asn Ser Asp Glu Leu Asp Ile Ser Ala Gly Asp Ile Leu Ala Val
         50                  55                  60

Ile Leu Glu Gly Glu Asp Gly Trp Trp Thr Val Glu Arg Asn Gly Gln
 65                  70                  75                  80

Arg Gly Phe Val Pro Gly Ser Tyr Leu Glu Lys Leu
                 85                  90

<210> SEQ ID NO 4
<211> LENGTH: 17
<212> TYPE: DNA
<213> ORGANISM: Homo sapiens

<400> SEQUENCE: 4
atgatgcccc agctgca                                                17

<210> SEQ ID NO 5
<211> LENGTH: 20
<212> TYPE: DNA
<213> ORGANISM: Homo sapiens

<400> SEQUENCE: 5
ccttctgcct ctcacgaaac                                             20

<210> SEQ ID NO 6
<211> LENGTH: 18
<212> TYPE: DNA
<213> ORGANISM: Homo sapiens

<400> SEQUENCE: 6
caaatggaga atgggcag                                               18
```

```
<210> SEQ ID NO 7
<211> LENGTH: 21
<212> TYPE: DNA
<213> ORGANISM: Homo sapiens

<400> SEQUENCE: 7
tggctttgtt ctgactcttc t                                              21

<210> SEQ ID NO 8
<211> LENGTH: 23
<212> TYPE: DNA
<213> ORGANISM: Homo sapiens

<400> SEQUENCE: 8
ccaagaagac atacgagcag aag                                            23

<210> SEQ ID NO 9
<211> LENGTH: 18
<212> TYPE: DNA
<213> ORGANISM: Homo sapiens

<400> SEQUENCE: 9
ccgcacttcc tcgtagag                                                  18

<210> SEQ ID NO 10
<211> LENGTH: 20
<212> TYPE: DNA
<213> ORGANISM: Homo sapiens

<400> SEQUENCE: 10
gcagtgtgtc aaggatgatg                                                20

<210> SEQ ID NO 11
<211> LENGTH: 19
<212> TYPE: DNA
<213> ORGANISM: Homo sapiens

<400> SEQUENCE: 11
gtctctgtgg acgcagcag                                                 19

<210> SEQ ID NO 12
<211> LENGTH: 21
<212> TYPE: DNA
<213> ORGANISM: Homo sapiens

<400> SEQUENCE: 12
tgccctacca gaactattac g                                              21

<210> SEQ ID NO 13
<211> LENGTH: 18
<212> TYPE: DNA
<213> ORGANISM: Homo sapiens

<400> SEQUENCE: 13
ccacagtcca ccagccat                                                  18

<210> SEQ ID NO 14
<211> LENGTH: 19
<212> TYPE: DNA
<213> ORGANISM: Homo sapiens

<400> SEQUENCE: 14
cagcgcagaa cccagatga                                                 19
```

-continued

```
<210> SEQ ID NO 15
<211> LENGTH: 20
<212> TYPE: DNA
<213> ORGANISM: Homo sapiens

<400> SEQUENCE: 15
agaacagaac gcactccttt                                                20

<210> SEQ ID NO 16
<211> LENGTH: 19
<212> TYPE: DNA
<213> ORGANISM: Homo sapiens

<400> SEQUENCE: 16
cacaatggcc tgtgaggag                                                 19

<210> SEQ ID NO 17
<211> LENGTH: 18
<212> TYPE: DNA
<213> ORGANISM: Homo sapiens

<400> SEQUENCE: 17
cgtgctcttg gcctggat                                                  18

<210> SEQ ID NO 18
<211> LENGTH: 1428
<212> TYPE: DNA
<213> ORGANISM: Homo sapiens
<220> FEATURE:
<221> NAME/KEY: CDS
<222> LOCATION: (1)..(1248)

<400> SEQUENCE: 18 atg atg ccc cag ctg cag ttc aaa gat gcc ttt tgg tgc agg gac ttc      48
Met Met Pro Gln Leu Gln Phe Lys Asp Ala Phe Trp Cys Arg Asp Phe
  1               5                  10                  15 aca gcc cac acg ggc tac gag gtg ctg ctg cag cgg ctt ctg gat ggc      96
Thr Ala His Thr Gly Tyr Glu Val Leu Leu Gln Arg Leu Leu Asp Gly
                 20                  25                  30 agg aag atg tgc aaa gac atg gag gag cta ctg agg cag agg gcc cag     144
Arg Lys Met Cys Lys Asp Met Glu Glu Leu Leu Arg Gln Arg Ala Gln
             35                  40                  45 gcg gag gag cgg tac ggg aag gag ctg gtg cag atc gca cgg aag gca     192
Ala Glu Glu Arg Tyr Gly Lys Glu Leu Val Gln Ile Ala Arg Lys Ala
         50                  55                  60 ggt ggc cag acg gag atc aac tcc ctg agg gcc tcc ttt gac tcc ttg     240
Gly Gly Gln Thr Glu Ile Asn Ser Leu Arg Ala Ser Phe Asp Ser Leu
 65                  70                  75                  80 aag cag caa atg gag aat gtg ggc agc tca cac atc cag ctg gcc ctg     288
Lys Gln Gln Met Glu Asn Val Gly Ser Ser His Ile Gln Leu Ala Leu
                 85                  90                  95 acc ctg cgt gag gag ctg cgg agt ctc gag gag ttt cgt gag agg cag     336
Thr Leu Arg Glu Glu Leu Arg Ser Leu Glu Glu Phe Arg Glu Arg Gln
                100                 105                 110 aag gag cag agg aag aag tat gag gcc gtc atg gac cgg gtc cag aag     384
Lys Glu Gln Arg Lys Lys Tyr Glu Ala Val Met Asp Arg Val Gln Lys
            115                 120                 125 agc aag ctg tcg ctc tac aag aag gcc atg gag tcc aag aag aca tac     432
Ser Lys Leu Ser Leu Tyr Lys Lys Ala Met Glu Ser Lys Lys Thr Tyr
        130                 135                 140 gag cag aag tgc cgg gac gcg gac gac gcg gag cag gcc ttc gag cgc     480
Glu Gln Lys Cys Arg Asp Ala Asp Asp Ala Glu Gln Ala Phe Glu Arg
```

```
                145                 150                 155                 160
att agc gcc aac ggc cac cag aag cag gtg gag aag agt cag aac aaa              528
Ile Ser Ala Asn Gly His Gln Lys Gln Val Glu Lys Ser Gln Asn Lys
                165                 170                 175 gcc agg cag tgc aag gac tcg gcc acc gag gca gag cgg gta tac agg              576
Ala Arg Gln Cys Lys Asp Ser Ala Thr Glu Ala Glu Arg Val Tyr Arg
            180                 185                 190 cag agc att gcg cag ctg gag aag gtc cgg gct gag tgg gag cag gag              624
Gln Ser Ile Ala Gln Leu Glu Lys Val Arg Ala Glu Trp Glu Gln Glu
        195                 200                 205 cac cgg acc acc tgt gag gcc ttt cag ctg caa gag ttt gac cgg ctg              672
His Arg Thr Thr Cys Glu Ala Phe Gln Leu Gln Glu Phe Asp Arg Leu
    210                 215                 220 acc att ctc cgc aac gcc ctg tgg gtg cac agc aac cag ctc tcc atg              720
Thr Ile Leu Arg Asn Ala Leu Trp Val His Ser Asn Gln Leu Ser Met
225                 230                 235                 240 cag tgt gtc aag gat gat gag ctc tac cag gaa gtg cgg ctg acg ctg              768
Gln Cys Val Lys Asp Asp Glu Leu Tyr Gln Glu Val Arg Leu Thr Leu
                245                 250                 255 gaa ggc tgc agc ata gac gcc gac atc gac agt ttc atc cag gcc aag              816
Glu Gly Cys Ser Ile Asp Ala Asp Ile Asp Ser Phe Ile Gln Ala Lys
            260                 265                 270 agc acg ggc aca gag ccc ccc gct ccg gtg ccc tac cag aac tat tac              864
Ser Thr Gly Thr Glu Pro Pro Ala Pro Val Pro Tyr Gln Asn Tyr Tyr
        275                 280                 285 gat cgg gag gtc acc ccg ctg acc agc agc cct ggc ata cag ccg tcc              912
Asp Arg Glu Val Thr Pro Leu Thr Ser Ser Pro Gly Ile Gln Pro Ser
    290                 295                 300 tgc ggc atg ata aag agg ttc tct gga ctg ctg cac gga agt ccc aag              960
Cys Gly Met Ile Lys Arg Phe Ser Gly Leu Leu His Gly Ser Pro Lys
305                 310                 315                 320 acc act tcg ttg gca gct tct gct gcg tcc aca gag acc ctg acc ccc             1008
Thr Thr Ser Leu Ala Ala Ser Ala Ala Ser Thr Glu Thr Leu Thr Pro
                325                 330                 335 acc ccc gag cgg aat gag ggt gtc tac aca gcc atc gca gtg cag gag             1056
Thr Pro Glu Arg Asn Glu Gly Val Tyr Thr Ala Ile Ala Val Gln Glu
            340                 345                 350 ata cag gga aac ccg gcc tca cca gcc cag gag tac cgg gcg ctc tac             1104
Ile Gln Gly Asn Pro Ala Ser Pro Ala Gln Glu Tyr Arg Ala Leu Tyr
        355                 360                 365 gat tat aca gcg cag aac cca gat gag ctg gac ctg tcc gcg gga gac             1152
Asp Tyr Thr Ala Gln Asn Pro Asp Glu Leu Asp Leu Ser Ala Gly Asp
    370                 375                 380 atc ctg gag gtg atc ctg gaa ggg gag gat ggc tgg tgg act gtg gag             1200
Ile Leu Glu Val Ile Leu Glu Gly Glu Asp Gly Trp Trp Thr Val Glu
385                 390                 395                 400 agg aac ggg cag cgt ggc ttc gtc cct ggt tcc tac ctg gag aag ctt             1248
Arg Asn Gly Gln Arg Gly Phe Val Pro Gly Ser Tyr Leu Glu Lys Leu
                405                 410                 415 tgaggaaggg ccaggagccc cttcggacct gccctgccag tggagccagc agtgccccca           1308
gcactgtccc caccttgcta gggcccagaa ccaagcgtcc cccagccccg agagggagcc           1368
tgtcgtctcc cagggaataa aggagtgcgt tctgttctaa aaaaaaaaaa aaaaaaaaaa           1428

<210> SEQ ID NO 19
<211> LENGTH: 416
<212> TYPE: PRT
<213> ORGANISM: Homo sapiens

<400> SEQUENCE: 19
```

-continued

```
Met Met Pro Gln Leu Gln Phe Lys Asp Ala Phe Trp Cys Arg Asp Phe
 1               5                  10                  15

Thr Ala His Thr Gly Tyr Glu Val Leu Leu Gln Arg Leu Leu Asp Gly
                 20                  25                  30

Arg Lys Met Cys Lys Asp Met Glu Glu Leu Leu Arg Gln Arg Ala Gln
             35                  40                  45

Ala Glu Glu Arg Tyr Gly Lys Glu Leu Val Gln Ile Ala Arg Lys Ala
         50                  55                  60

Gly Gln Thr Glu Ile Asn Ser Leu Arg Ala Ser Phe Asp Ser Leu
 65                  70                  75                  80

Lys Gln Gln Met Glu Asn Val Gly Ser Ser His Ile Gln Leu Ala Leu
                 85                  90                  95

Thr Leu Arg Glu Glu Leu Arg Ser Leu Glu Glu Phe Arg Glu Arg Gln
                100                 105                 110

Lys Glu Gln Arg Lys Lys Tyr Glu Ala Val Met Asp Arg Val Gln Lys
            115                 120                 125

Ser Lys Leu Ser Leu Tyr Lys Lys Ala Met Glu Ser Lys Lys Thr Tyr
        130                 135                 140

Glu Gln Lys Cys Arg Asp Ala Asp Asp Ala Glu Gln Ala Phe Glu Arg
145                 150                 155                 160

Ile Ser Ala Asn Gly His Gln Lys Gln Val Glu Lys Ser Gln Asn Lys
                165                 170                 175

Ala Arg Gln Cys Lys Asp Ser Ala Thr Glu Ala Glu Arg Val Tyr Arg
                180                 185                 190

Gln Ser Ile Ala Gln Leu Glu Lys Val Arg Ala Glu Trp Glu Gln Glu
            195                 200                 205

His Arg Thr Thr Cys Glu Ala Phe Gln Leu Gln Glu Phe Asp Arg Leu
        210                 215                 220

Thr Ile Leu Arg Asn Ala Leu Trp Val His Ser Asn Gln Leu Ser Met
225                 230                 235                 240

Gln Cys Val Lys Asp Asp Glu Leu Tyr Gln Glu Val Arg Leu Thr Leu
                245                 250                 255

Glu Gly Cys Ser Ile Asp Ala Asp Ile Asp Ser Phe Ile Gln Ala Lys
                260                 265                 270

Ser Thr Gly Thr Glu Pro Pro Ala Pro Val Pro Tyr Gln Asn Tyr Tyr
            275                 280                 285

Asp Arg Glu Val Thr Pro Leu Thr Ser Ser Pro Gly Ile Gln Pro Ser
        290                 295                 300

Cys Gly Met Ile Lys Arg Phe Ser Gly Leu Leu His Gly Ser Pro Lys
305                 310                 315                 320

Thr Thr Ser Leu Ala Ala Ser Ala Ala Ser Thr Glu Thr Leu Thr Pro
                325                 330                 335

Thr Pro Glu Arg Asn Glu Gly Val Tyr Thr Ala Ile Ala Val Gln Glu
                340                 345                 350

Ile Gln Gly Asn Pro Ala Ser Pro Ala Gln Glu Tyr Arg Ala Leu Tyr
            355                 360                 365

Asp Tyr Thr Ala Gln Asn Pro Asp Glu Leu Asp Leu Ser Ala Gly Asp
        370                 375                 380

Ile Leu Glu Val Ile Leu Glu Gly Glu Asp Gly Trp Trp Thr Val Glu
385                 390                 395                 400

Arg Asn Gly Gln Arg Gly Phe Val Pro Gly Ser Tyr Leu Glu Lys Leu
                405                 410                 415
```